United States Patent
Silver

(10) Patent No.: US 6,303,155 B1
(45) Date of Patent: *Oct. 16, 2001

(54) TREATMENT OF CONDITIONS ASSOCIATED WITH IMPAIRMENT IN THE LEVEL OF THE PARATHYROID HORMONE

(75) Inventor: Justin Silver, Motza Illit (IL)

(73) Assignee: Hadasit Medical Research Services and Development Company, Ltd., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/258,907

(22) Filed: Mar. 1, 1999

Related U.S. Application Data

(63) Continuation-in-part of application No. 08/601,989, filed on Feb. 15, 1996, now Pat. No. 5,935,607.

(51) Int. Cl.$^7$ ............................ A61K 33/42; A61K 33/06
(52) U.S. Cl. ......................... 424/601; 424/602; 424/603; 424/604; 424/605; 424/606; 424/682
(58) Field of Search ..................................... 424/601, 602, 424/603, 604, 605, 606, 682; 514/878

(56) References Cited

U.S. PATENT DOCUMENTS

| | | |
|---|---|---|
| 5,409,911 | 4/1995 | Tyler et al. . |
| 5,935,607 * | 8/1999 | Silver .................................... 424/601 |

OTHER PUBLICATIONS

Black et al., Timed therapy with calcium and phosphate supplements restores phosphate and parathyroid hormone rhythms in patients with osteoporosis, with an anabolic effect on spinal bone mineral density (1996), Journal of Endocrinology, vol. 148, Supp., P 192.*
Goodman and Gilman's The Pharmacological Basis of Therapeutics (6th Ed., 1980), pp. 1529–1535.*
Kishikawa et al., 'Diurnal changes in calcium and phosphate metabolism in rats' (Hormone and Metabolic Research, (1980) 12/10 (545–551)), STN/CAS online, file EMBASE, abstract.*
Woo et al., 'Biochemical effects of a single dose of calcium on bone metabolism in elderly Chinese women' (Calcified Tissue International, (1991) 48/3 (157–160)), STN/CAS online, file EMBASE, abstract.*
Silverberg et al., 'The effect of oral phosphate administration on major indexes of skelatal metabolism in normal subjects' (J. Bone Miner. Res. (1986), 1(4), 383–8), STN/CAS online, file CAPLUS, abstract.*
Remington's Pharmaceutical Sciences (17th Ed., 1985), pp. 1768, 1774, 1786–1789.*
STN/CAS online, file EMBASE, Acc. No. 92365999, Doc. No. 1992365999, (Herfarth et al., 'Circadian rhythm and pulsatility of parathyroid hormone secretion in man', Clinical Endocrinology (1992), 37/6, pp. 511–519), Abstract.*

Dube et al., 'Circadian rhythmicity of serum parathyroid hormone in man: Role of phosphate and ionized calcium', Clin. Res. (1972), vol. 20, No. 3, p. 425.*
Calvo et al., 'Circadian variation in ionized calcium and intact parathyroid hormone: Evidence for sex differences in calcium homeostatis', J. Clin. Endocrinol. Metab. (1991), vol. 72, No. 1, pp. 69–76.*
Sinha et al., 'Demonstration of a diurnal variation in serum parathyroid hormone in primary and secondary hyperparathyroidism', J. Clin. Endocrinol. Metab. (1975), vol. 41, No. 6, pp. 1009–1013.*
Silver et al., Parathyroid Hormone–Molecular Biology and Regulation, Principles of Bone Biology, Chapter 24, pp. 325–337.
Hebert et al., Studies of the Mechanism by Which Phosphate Infusion Lowers Serum Calcium Concentration, Journal of Clinical Investigation, vol. 45, No. 12, 166, pp. 1886–1894.
Marie et al., Mechanisms Underlying the Effects of Phosphate and Calcitonin on Bone Histology in Postmenopausal Osteoporosis, Bone, vol. 7, 1986, pp. 17–22.
Kilev et al., Parathyroid Hormone Gene Expression in Hypophosphatemic Rats, The Journal of Clinical Investigation, vol. 96, No. 1, 1995, pp. 327–333.
Prank et al., Time Series Prediction of Plasma Hormone Concentration, Time Series Prediction of Plasma Hormone Concentration, pp. 2910–2919.
Naveh–Many, Estrogen Receptors and Biologic Response in Rat Parathyroid Tissue and C Cells, J. Clin. Invest, vol. 90, 1992, pp. 2434–2438.
Rodan, Mechanical Loading, Estrogen Deficiency, and the Coupling of Bone Formation to Bone Resorption, Journal of Bone and Mineral Research, vol. 6, No. 6, 1991, pp. 527–530.
Juppner et al., A G Protein–Linked Receptor for Parathyroid Hormone and Parathyroid Hormone–Related Peptide, Science, vol. 254, pp. 1024–1026.
Mosekilde et al., The Anabolic Effects of Parathyroid Hormone on Cortical Bone Mass, Dimensions and Strength–Assessed in a Sexually Mature, Ovariectomized Rat Model, Elsevier Science, Inc., 1995, pp. 223–230.

(List continued on next page.)

Primary Examiner—Jose' G. Dees
Assistant Examiner—Frank Choi
(74) Attorney, Agent, or Firm—Browdy and Neimark

(57) ABSTRACT

A method for restoration of the circadian rhythm of parathyroid hormone (PTH) serum levels in a subject having osteoporosis, so as to restore a circadian rhythm of PTH levels which is similar to that existing in normal subjects is disclosed by administering a single daily dose of a composition consisting essentially of an effective amount of phosphate in the evening or at night, whereby the composition causes a circadian rhythm of PTH levels which peaks during the night, whereby the circadian rhythm of PTH levels is restored to that which is similar to that existing in normal subjects, thereby treating osteoporosis.

7 Claims, 3 Drawing Sheets

OTHER PUBLICATIONS

Reeve et al., Anabolic effect of human parathyroid hormone fragment ontrabecular bone in involutional osteoporosis: a multicentre trial, British medical Journal, 1980, pp. 1340–1344.

Dempster et al., Anabolic Actions of Parathyroid Hormone on Bone, The Endocrine Society, vol. 14, 1993, pp. 691–709.

Finkelstein et al., Parathyroid Hormone for the Prevention of Bone Loss Induced by Estrogen Deficiency, The New England Journal of medicine, vol. 331, No. 24, 1994, pp. 1618–1624.

Silver et al., Regulation by Vitamin D Metabolites of Parathyroid Hormone Gene Transcription in Vivo in the Rat, J. Clin. Invest., vol. 78, 1986, pp. 1296–1301.

Okazakit et al., A Redox Factor Protein, ref1, Is Involved in Negative Gene Regulation by Extracellular Calcium, The Journal of Biological Chemistry, 1994, vol. 269, No. 45, pp. 27855–27862.

Pe'er et al., PC–10 Immunostaining of Proliferating Cell Nuclear Antigen in Posterior Uveal Melanoma, pp. 56–62.

Gavrieli et al., Identification of Programmed Cell Death In Situ via Specific Labeling of Nuclear DNA Fragmentation, The Jour. of Cell Biology, vol. 119, No. 3, 1992, pp. 493–501.

* cited by examiner

TREATMENT OF CONDITIONS ASSOCIATED WITH IMPAIRMENT IN THE LEVEL OF THE PARATHYROID HORMONE

This is a continuation-in-part application of U.S. Ser. No. 08/601,989, filed Feb. 15, 1996, U.S. Pat. No. 5,935,607 herein incorporated by reference in its entirety.

FIELD OF THE INVENTION

The present invention is generally in the field of endocrinology and treatment of conditions associated with impairment in normal hormone levels. More specifically, the present invention provides a composition and method for increasing the level of the parathyroid hormone (PTH) in a needy subject. In accordance with a preferred embodiment, the method and composition are used for the treatment of osteoporosis.

PRIOR ART

The following is a list of prior art believed to be relevant as a background of the invention:

1. Rodan, G. A., Mechanical loading, estrogen deficiency, and the coupling of bone formation to bone resorption, *J. Bone Miner. Res.*, 6:527–530, 1991.
2. Juppner, H., Abou-Samra, A. B., Freeman, M., Kong, X. F., Schipani, E., Richards, J., Kolakowski, L. F., Hock, J., Potts, J. T., Kronenberg, H. M., and Segre, G. V., A G-protein-linked receptor for parathyroid hormone and parathyroid hormone-related peptide, *Science*, 254:1024–1026, 1991.
3. Mosekilde, Li, Danielsen, C. C., Sogaard, C. H., McOsker, J. E., and Wronski, T. J., The anabolic effects of parathyroid hormone on cortical bone mass, dimensions and strength-assessed in a sexually mature, ovariectomized rat model, *Bone*, 16:223–230, 1995.
4. Reeve, J., Meunier, P. J., Parsons, J. A., Bernat, M., Bilvoet, O. L. M., Courpron, P., Edouard, C., Klenerman, L., Neer, R. M., Renier, J. C., Slovik, D., Vismans, F. J. F. E., and Potts, J. T., Anabolic effects of human parathyroid hormone fragment on trabecular bone in involutional osteoporosis: A multicentre trial, *Br. Med. J.*, 280:1340–1344, 1980.
5. Dempster, D. W., Cosman, F., Parisien, M., Shen, V., and Lindsay, R., Anabolic actions of parathyroid hormone on bone, *Endocrine Rev.*, 14:690–709, 1993.
6. Finkelstein, J. S., Klibanski, A., Schaeffer, E. H., Hornstein, M. D., Schiff, I., and Neer, R. M., Parathyroid hormone for the prevention of bone loss induced by estrogen deficiency, *New Eng. J. Med.*, 331:1618–1623, 1994.
7. Prank, S., Nowlan, S. J., Harms, H. M., Kloppstech, M., Brabant, G., Hesch, R. D., and Sejnowski, T. J., Time series prediction of plasma hormone concentration. Evidence for differences in predictability of parathyroid hormone secretion between osteoporotic patients and normal controls, *J. Clin. Invest.*, 95:2910–2919, 1995.

Acknowledgement of the above references herein will be made by indicating their number from the above list.

BACKGROUND OF THE INVENTION

Osteoporosis results in bone fractures in about 50% of postmenopausal women and is a leading cause of disability in an aging population. Current therapies include an adequate calcium and vitamin D intake as well as specific treatment with compounds such as estrogens, calcitonin and the bisphosphonates[1]. However, each of these treatments has either troubling side effects or limited efficacy. Women fear the small increase in breast cancer due to estrogens despite the dramatic reduction in myocardial infarctions and reduction in bone resorption. Calcitonin has a limited effect and is a protein and therefore needs to be injected or inhaled which is inconvenient. The new bisphosphonates such as alendronate have had encouraging results with an increase in bone density and decrease in fractures with few side effects. Current research for new compounds has concentrated on the systemic administration of bone anabolic compounds such as parathyroid hormone (PTH) or fragments of PTH or locally acting cytokines or bone growth factors such as bone morphogenic proteins. The appeal of PTH is that there are specific PTH receptors in bone[2] and it is well established in both experimental animal[3] and patient studies that intermittent doses of injected PTH is the most effective agent known to increase bone formation and bone strength[4-6]. This effect is additive to that of estrogens. The problem with the administration of PTH is that it is a peptide and must therefore be given by injection. Women with osteoporosis have intact but inadequately functioning parathyroids and an alternative approach is to stimulate their own parathyroids to synthesize and secrete more PTH. It has been evidenced in experimental animals that this is eminently practicable and this is the basis of this present patent application.

Postmenopausal osteoporotic women do not have the appropriate increase in nocturnal serum PTH levels. In osteoporotic women, careful and repeated measurements of serum PTH, and analysis by time series prediction of plasma hormone concentration has shown that there are differences in the predictability of parathyroid hormone secretion between postmenopausal osteoporotic patients and postmenopausal non-osteoporotic controls[7].

SUMMARY OF THE INVENTION

It is the object of the present invention to provide a method and composition for increase in PTH levels in needy subjects.

It is an object in accordance with a preferred embodiment of the invention to provide such a method allowing to restore a circadian rhythm of PTH serum levels similar to that existing in normal individuals.

It is an objection in accordance with another preferred embodiment of the invention to provide a composition and method for the treatment of osteoporosis.

These and other objects of the invention will become clear from the description below.

In accordance with the present invention, it has been found that administration of phosphate results in an increase in PTH levels. Furthermore, in accordance with the invention, the phosphate is preferably administered to individuals in the evening or at night, giving rise to increase in PTH levels during night time, as is the case in normal individuals.

The present invention thus provides novel means for the treatment of individuals suffering from conditions resulting from impairment in PTH levels, by the administration of phosphate. The treatment has utility both in human and veterinary medicine.

The present invention thus provides a method of treatment of conditions resulting from impairment in parathyroid hormone (PTH) levels, comprising administering to a subject in need an effective amount of phosphate.

The present invention also provides a composition for use in treatment of conditions in subjects resulting from impairment in parathyroid hormone (PTH) levels, such as osteoporosis comprising an effective amount of phosphate together with a physiologically acceptable carrier.

The present invention still further provides use of phosphate for the preparation of compositions for the treatment of conditions in subjects resulting from impairment in PTH levels.

In accordance with a preferred embodiment of the invention, the phosphate is administered to individuals at night, and this administration forms part of a combined treatment involving also a timed administration of an effective amount of an auxiliary agent, e.g. calcium, which is capable of decreasing the PTH level during day time. Such an agent may typically be administered to the individual in the morning, and also once again during the day. As a result of such a combined treatment, PTH will have a low level during day time and a higher level during night time, giving rise to a circadian profile of PTH levels, similar to that existing in normal individuals.

The term "effective amount" used above, should be understood as meaning an amount of an active ingredient, i.e. phosphate or an auxiliary agent, which is capable of exerting a desired therapeutic effect. In the case of phosphate, an effective amount is an amount sufficient to cause an increase in the PTH levels; in the case of said auxiliary agent, an effective amount is an amount sufficient to cause a decrease in PTH levels. As will be clear, an effective amount may at times vary between different groups of individuals depending on the factors such as age, type of treated condition, etc., as will no doubt be clear to the artisan.

DETAILED DESCRIPTION OF THE INVENTION

The present invention provides novel means for the treatment of conditions associated with reduction in PTH levels. Such conditions include in particular osteoporosis. In the following, the invention will be described with specific reference to the treatment of osteoporosis, it being understood that it applies, mutatis mutandis, also to treatment or other conditions.

Osteoporosis, as noted above, is a condition which appears primarily in postmenopausal women, and at times also in men, which results, primarily, from decrease in PTH levels. In addition to reduction in the PTH level, osteoporosis is also associated with impairment of the normal circadian rhythm of PTH—low levels during day time and higher levels at night.

In accordance with the invention, phosphate is used for increasing the level of PTH in needy individuals. The phosphate may be administered to individuals in the form of a salt, e.g. a sodium or a potassium salt, either in their neutral or acid forms. The phosphate may be administered in the form of pills, capsules, a liquid, drinkable solution, etc. At times, the phosphate may also be administered parenterally, e.g. within a saline solution, although it will be appreciated that such form of administration, particularly since it is needed on a daily basis, is less physiologically tolerable.

An effective amount of phosphate is typically within the range of about 2–50 mg/kg body weight, preferably with the range of about 5–30 mg/kg body weight, most preferably in the range of 10–30 mg/kg. Thus for a person weighing about 50 kg the total dose ranges from 100–2500 mg, preferably 150–1500 mg, most preferably 500–1500 mg. For a person weighing about 80 kg the total dose ranges from 160–4000 mg, preferably 400–2400 mg, most preferably 800–2400 mg.

In accordance with a preferred embodiment of the invention, phosphate is administered to needy individuals in the evening or night, e.g. prior to bedtime.

In accordance with a specifically preferred embodiment such as treatment is accompanied by the administration of said auxiliary agent, e.g. calcium during day time. Calcium can be administered for example, once in the early morning hours and once during mid-day. Such administration of calcium will maintain a relatively low level of PTH during day time. An effective amount of calcium may for example be about 5–20 mg/kg body weight, preferably about 6–15 mg/kg body weight and most desirably about 6–10 mg/kg body weight. Calcium may be administered to individuals, as known, per se, in the form of a pill, in the form of a drink, e.g. prior prepared from an effervescent calcium preparation, etc.

Calcium and phosphate preparations for administration to individuals may be provided together in a single package, at times accompanied by instructions for use in an administration regimen in accordance with the combined treatment of the invention. Typically, such a package will comprise daily dosage forms of each of these active agents. For example, the package may comprise two calcium tablets and one phosphate tablet for each day, the two calcium tablets intended and marked so as to be taken by the individual in the morning and at mid-day, and the phosphate pill intended and marked so as to be taken by the individual prior to bed time.

The invention will now be illustrated in the following examples describing experiments carried out in accordance with the invention. In these examples reference will at times be made to the annexed drawings.

METHODS

I. Animals

Figure 1:
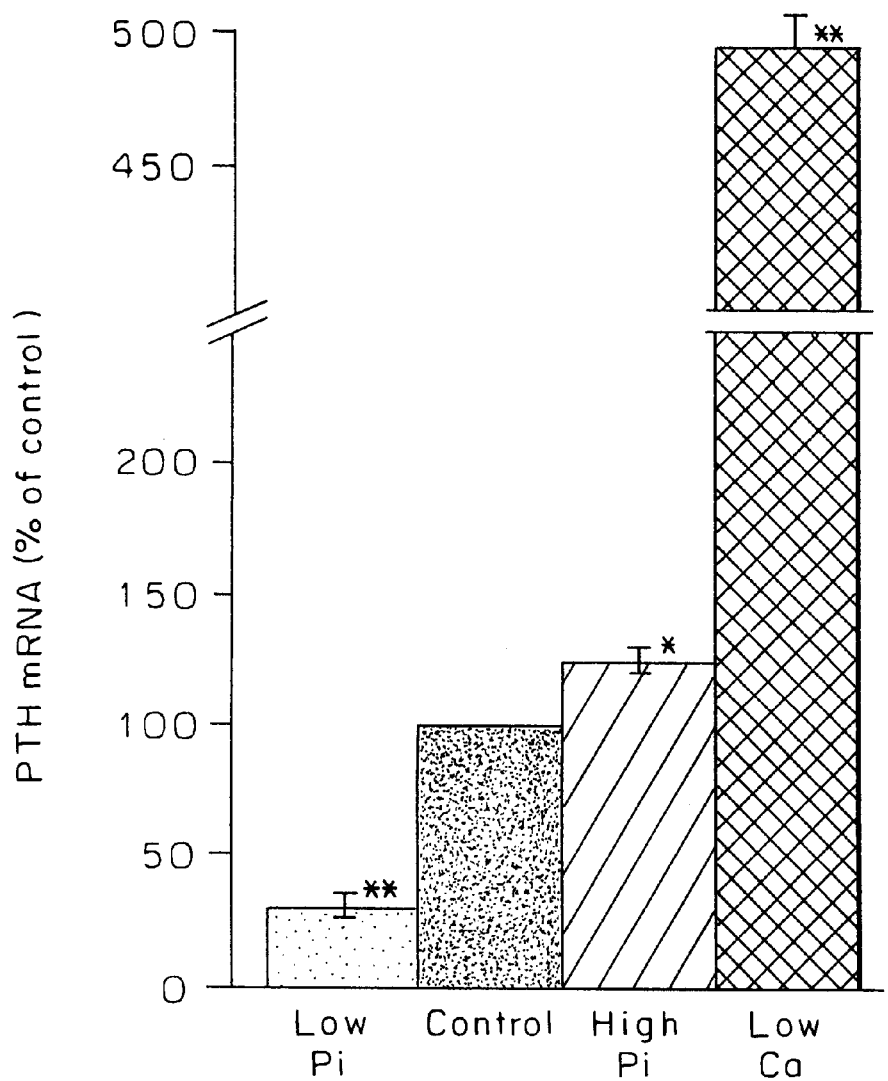
FIG. 1 shows the effect of dietary phosphate and calcium on PTH mRNA levels. Results are shown for weanling rats fed diets for three weeks containing low phosphate (0.02%); control untreated rats; high phosphate (1.2%); low calcium (0.02%); as means±SEM for four rats and compared to rats fed the control diet—*$P<0.05$; **$P<0.01$.
Figure 2A:
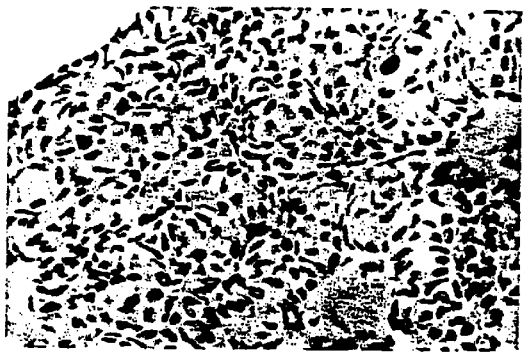
FIGS. 2a–d shows PCNA staining of parathyroid tissue from rats fed diets with a low calcium or phosphate, or after treatment with 1,25(OH)$_2$D$_3$. PCNA-positive nuclei are stained red: (1) a control rat 10 days after weaning; (2) a rat fed a low calcium diet for 10 days; (3) a rat fed a low phosphate diet for 21 days; (4) a rat injected i.p. with 1,25(OH)$_2$D$_3$ (25 pmol/d for 3 days)
Figure 2B:
Figure 2C:
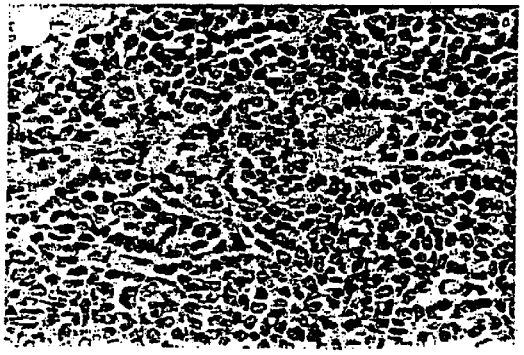
Figure 2D:
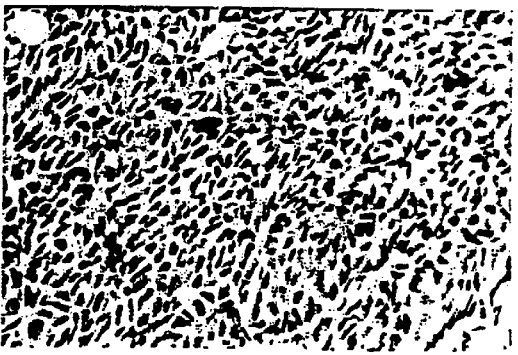

Weanling male Hebrew University strain rats were maintained for 3 weeks on the following diets (Teklad, Ill.): Low phosphate, normal calcium (0.02% phosphate, 0.6% calcium); normal phosphate, normal calcium (0.3% phosphate, 0.6% calcium); high phosphate, high calcium (1.2% phosphate; 1.2% calcium); vitamin D deficient, low calcium (0.02% calcium). After 1 to 21 days the thyroparathyroid tissue was excised under pentobarbital anesthesia, and blood samples taken. All rat surgery was performed at 9–10 a.m. The excised tissue was immediately frozen in liquid nitrogen and stored at −70° C.

II. Measurement of cellular mRNA levels

RNA was extracted from rat thyroparathyroid tissue and the levels of PTH mRNA were measured by Northern blots after extraction with TRI Reagent (Molecular Research Center Inc., Cincinnati, Ohio). RNA was denatured and ethidium bromide was added to each sample at a concentration of 0.1 mg/ml. The samples were size-fractionated by electrophoresis on 1.25% agarose gels containing formaldehyde and transferred to Hybond filters (Amersham, England) by diffusion blotting. The integrity of the RNA and the uniformity of RNA transfer to the membrane were determined by UV visualization of the ribosomal RNA bands of the gels and the filters. The filters were fixed by UV cross-linking and hybridized as previously described (Naveh-Many et al., *J. Clin. Inves.*, 90:2434–2438 (1992); Silver et al., *J. Clin. Inves.*, 78:1296–1301 (1986)). Hybridization was to a random primed rat PTH cDNA (a gift of H. Meyer, GBF, Braunschweig, Germany) and 18S RNA (gift of Mr. A. Levine, Baltimore, Md.).

III. Immunohistochemistry

Proliferating cell nuclear antigen (PCNA).

Paraffin tissue blocks were cut to 4–6 mm-thick sections, deparaffinized in xylene and alcohols, and placed for 15 mins. in alcohol-$H_2O_2$, 3%, for blocking endogenous peroxidase. To reveal masked antigens in formalin-fixed, paraffin-embedded tissue sections, slides were placed in citrate buffer (pH 6.0) and treated in the microwave at 92° C. for 10 mins. After removing container from the microwave and cooling for 15 mins, slides were placed in PBS (pH 7.6). Sections were then treated with Bovine Serum Albumin (BSA) to prevent background staining, and incubated for one hour with the primary antibody PCNA-PC-10 (Zymed Laboratories, Inc., San Francisco, Calif.) at room temperature in a humidified chamber (Okazaki et al., *J. Biol. Chem.*, 269:27855–62 (1994); Peer et al., *Ophthalmology*, 101:56–62 (1994)). Slides were rinsed with PBS for 3–4 mins. and incubated with the biotinylated linked antibody for 30 mins. and with the labeling reagent peroxidase conjugated streptavidin for 30 mins. (Bio Genex Laboratories, San Ramon, Calif.). After rinsing, the peroxidase label was demonstrated using 3-amino-9-ethyl carbazole (AEC) for 15 mins., and counterstained with Mayer Hematoxylin. AEC produces a red end-product that is soluble in alcohol and is used with an aqueous mounting media (Kaiser's glycerol gelatin). A negative control was run using the same technique but omitting the primary antibody and adding the streptavidin-biotin complex. PCNA positive cells were counted per microscope field with the PT section completely filling the microscope field. For each rat four microscope fields were counted and the mean used. The variation amongst sections in each rat was always<10%. Each group represents the mean±SEM of 4–5 rats.

IV. DNA nick end labeling of tissue sections

This was performed essentially as described (Gavrieli et al., *J. Cell Biol.*, 119:493–501 (1992)). Tissue sections were treated with proteinase K, washed four times, treated with 2% $H_2O_2$, rinsed and immersed in buffer with biotinylated dUTP and rinsed. The sections were covered with Extra-avidin peroxidase (BioMakor, Rehovot, Isreal), washed and stained with AEC for 30 mins. (Gavrieli et al., supra).

V. Serum measurements

Serum calcium and phosphate were measured in a Roche autoanalyzer. Serum $1,25(OH)_2D_3$, levels were measured by a radioreceptor assay (Incstar, Minneapolis, Minn.). Serum iPTH levels were measured with a rat immunoradiomimetric assay (Nichols, San Clemente, Calif.). Statistical analysis was performed on the Macintosh program Statview 512+, using Student's unpaired two-tailed t test. The results are presented as the mean±SEM.

EXAMPLE 1

Serum Biochemistry of Animals Fed With Different Diets

The biochemistry of serum calcium, serum phosphate and serum $1,25(OH)_2D_3$ of animals fed with low calcium, low phosphate and high phosphate is shown in Table 1.

TABLE 1

The effects of 3 weeks of diet given to weanling rats

| Diet | Serum calcium (means ± SE) mg/dl | Serum phosphate (mean ± SE) mg/dl | Serum 1.25 $(OH)_2D_3$ (means ± SE) pg/ml |
|---|---|---|---|
| Control | 10.6 ± 0.6 | 9.8 ± 1.2 | 68.0 ± 28.3 |
| Low calcium | 6.8 ± 0.1† | 9.9 ± 0.5 | >400† |
| Low phosphate | 12.6 ± 0.6‡ | 4.0 ± 0.4† | >400† |
| High phosphate | 11.1 ± 0.6 | 9.4 ± 0.8 | 30.0 ± 5.9‡ |

Four Rats in each group:
‡P < 0.05 and
†P < 0.01 compared with control diet.

As can be seen serum calcium was decreased in the rats fed a low calcium diet and increased in rats fed a low phosphate diet. Serum phosphate only changed in the rats fed a low phosphate diet where it was decreased. Serum $1,25(OH)_2D_3$ was markedly increased in rats fed both the low calcium and the low phosphate diets, and decreased by the high phosphate diet.

EXAMPLE 2

PTH mRNA Levels of Animals Fed With Different Diets

Weanling animals were fed diets for three weeks containing low phosphate (0.02%), control normal diet; high phosphate (1.2%) and low calcium. The results are shown in FIG. 1. As can be seen, PTH mRNA levels were increased in the rats fed the low calcium diet and markedly decreased in the rats fed a low phosphate diet with no changes in a control gene 18 S RNA (not shown).

EXAMPLE 3

PCNA of Parathyroid Tissue From Rats Fed With Different Diets

Parathyroid tissue was obtained from four control untreated rats (1 FIG. 3); rats fed with low calcium (0.02%) for 10 days (2 FIG. 2); low phosphates (0.02%) for 21 days (3 FIG. 2); or rats injected i.p. w.t. $1,25(OH)_2D_3$ (25 pmol/d for 3 days) (4 FIG. 2) and the proliferating cell nucleus antigen (PCNA) was determined as described in (III) above.

Figure 3:
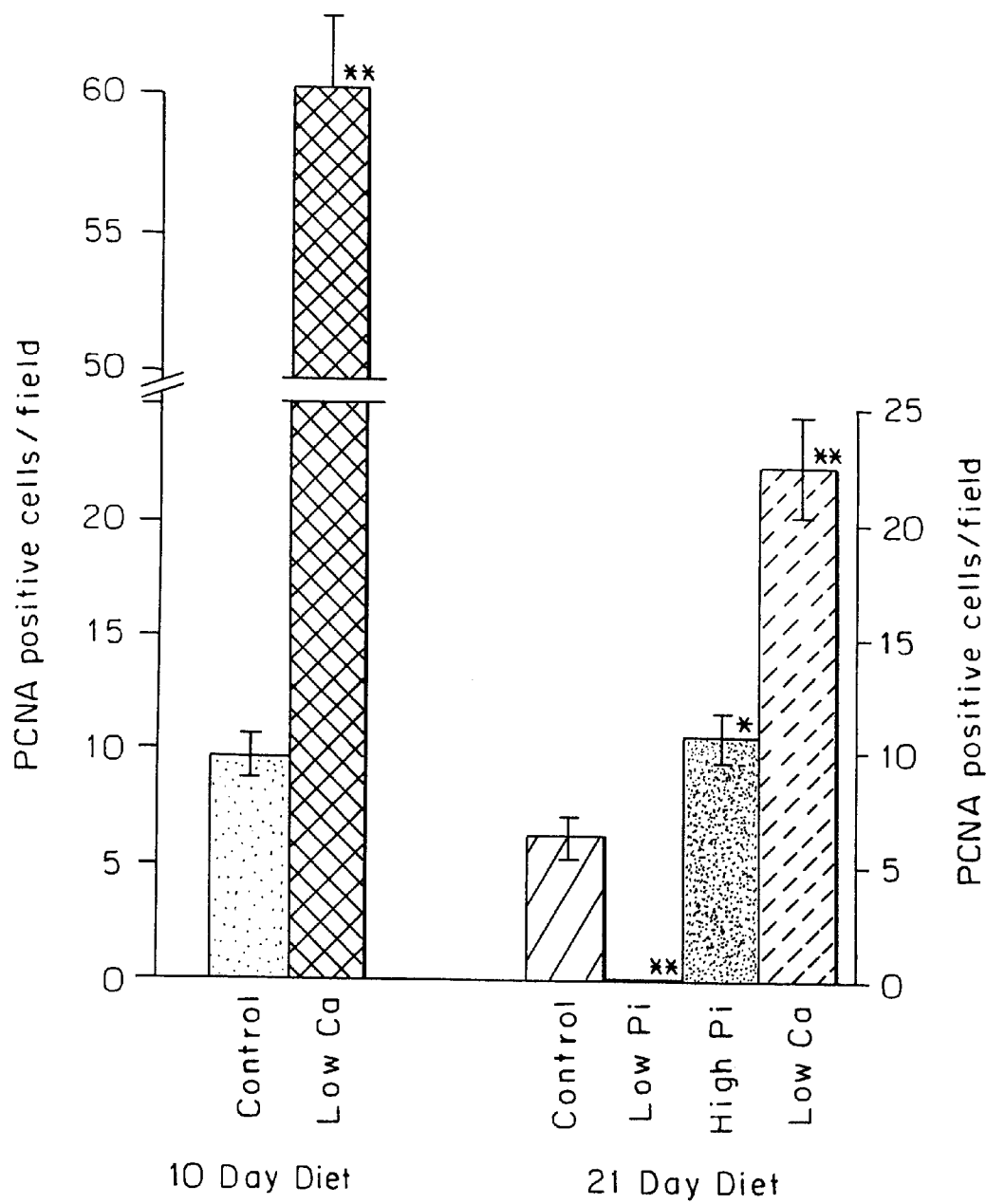
FIG. 3 shows the PCNA positive cell counts per field of rats fed control diet: low calcium (0.02%); low phosphate (0.02%); or high phosphate diet for 10 or 21 days. The results are expressed as PCNA positive cells per microscope field, as mean±SE for four different rats and compared to rats fed the control diet; *$P<0.05$; **$P<0.01$.

The results are shown in FIG. 2 (PCNA staining) or FIG. 3 (PCNA counts of positive cells per field). As can be seen, PCNA staining of thyroparathyroid tissue showed that there were~10 PCNA positive cells per microscope field in the PTs of a control rat 10 days after weaning and there was a sixfold increase in weanling rats fed a low calcium diet for 10 days (FIGS. 2 and 3). After 21 days of diet there was a smaller number of PCNA positive cells in the control rats ($P<0.05$) as compared with rats at 10 days after weaning and those rats on a low calcium diet had a 3.6-fold increase in PCNA positive cells (FIGS. 2 and 3). After a low phosphate diet for 21 days there were no PCNA positive cells at all (FIGS. 2 and 3) as well as a marked decrease in PTH mRNA levels (FIGS. 1 and 3). Rats fed a high phosphate diet had a moderate increase in PTH mRNA levels (FIGS. 1 and 3) and more PCNA positive cells than the controls, but not nearly as much as rats fed a low calcium diet (FIG. 3).

What is claimed is:

1. A method for restoration of the circadian rhythm of parathyroid hormone (PTH) serum levels in a subject having osteoporosis, so as to restore a circadian rhythm of PTH levels which is similar to that existing in normal subjects, comprising:

administering a single daily dose of a composition consisting essentially of an effective amount of phosphate in the evening or at night, prior to bedtime, whereby the composition causes a circadian rhythm of PTH levels which peaks during the night, whereby the circadian rhythm of PTH levels is restored to that which is similar to that existing in normal subjects, thereby treating the osteoporosis.

2. The method in accordance with claim 1, wherein said single daily dose is administered orally.

3. The method in accordance with claim 1, wherein said subject is a human subject.

4. The method in accordance with claim 1, further including the timed administration of an auxiliary agent capable of decreasing the PTH level, which administration is in the day time, whereby the result of the combined treatment is a rhythm of PTH which has a low level during the day time and a higher level during night time thereby giving rise to a circadian profile of PTH level similar to that existing in normal subjects.

5. The method in accordance with claim 4, wherein said auxiliary agent is calcium.

6. The method in accordance with claim 4, wherein said auxiliary agent is administered once in the early morning hours and once during mid-day.

7. The method in accordance with claim 1, wherein said phosphate is selected from the group consisting of sodium phosphate and potassium phosphate.

* * * * *